(12) United States Patent
Bilotti et al.

(10) Patent No.: US 6,978,922 B2
(45) Date of Patent: Dec. 27, 2005

(54) SURGICAL STAPLING INSTRUMENT

(75) Inventors: Federico Bilotti, Rome (IT); Mark Neurohr, Rome (IT); Laszlo Csiky, Piliseaszfalu (HU)

(73) Assignee: Ethicon Endo-Surgery (Europe) G.m.b.H., Norderstedt ( * ) Notice: Subject to any disclaimer, the term of this patent is extended or adjusted under 35 U.S.C. 154(b) by 0 days.

(21) Appl. No.: 10/287,067

(22) Filed: Nov. 4, 2002

(65) Prior Publication Data
US 2003/0178465 A1  Sep. 25, 2003

(51) Int. Cl.[7] .......................... A61B 17/04; A61B 17/10
(52) U.S. Cl. .............................. 227/180.1; 227/176.1; 227/181.1; 227/19
(58) Field of Search ................................ 227/181.1, 19, 227/180.1, 175.1, 176.1, 177.7, 179.1

(56) References Cited

U.S. PATENT DOCUMENTS

| | | | | |
|---|---|---|---|---|
| 3,078,465 A | * | 2/1963 | Sergueevitch | ................ 227/152 |
| 3,079,606 A | * | 3/1963 | Sergeevich et al. | ............ 227/76 |
| 3,771,526 A | * | 11/1973 | Rudie | .......................... 606/153 |
| 4,169,476 A | * | 10/1979 | Hiltebrandt | .................. 606/142 |
| 4,289,133 A | | 9/1981 | Rothfuss | |
| 4,290,542 A | * | 9/1981 | Fedotov et al. | .............. 227/155 |
| 4,752,024 A | * | 6/1988 | Green et al. | ................... 227/19 |
| 5,205,459 A | | 4/1993 | Brinkerhoff et al. | |
| 5,275,322 A | | 1/1994 | Brinkerhoff et al. | |
| 5,452,837 A | * | 9/1995 | Williamson | .............. 227/176.1 |
| 5,667,526 A | * | 9/1997 | Levin | .......................... 606/207 |
| 5,732,872 A | * | 3/1998 | Bolduc et al. | ............ 227/176.1 |
| 5,915,616 A | * | 6/1999 | Viola et al. | ............... 227/179.1 |
| 6,126,058 A | * | 10/2000 | Adams et al. | ........... 227/180.1 |
| 6,193,129 B1 | * | 2/2001 | Bittner et al. | ............. 227/180.1 |

FOREIGN PATENT DOCUMENTS

| | | |
|---|---|---|
| EP | 1090592 A1 | 4/2001 |
| RU | 122539 A | 7/1984 |
| WO | WO 01/54594 A1 | 1/2000 |

* cited by examiner

Primary Examiner—Scott A. Smith
Assistant Examiner—Brian Nash
(74) Attorney, Agent, or Firm—Dean Garner

(57) ABSTRACT

A surgical stapling instrument comprises a frame having a body portion and a handle. A staple fastening assembly is provided in the distal region of the instrument and includes a cartridge device, which comprises at least one closed row (10, 12) of staples, and an anvil. The anvil is movable relative to the cartridge device and is adapted to cooperate with the cartridge device for forming the ends of the staples exiting from the cartridge device. A knife, which has a closed cutting edge, is contained within the cartridge device and is positioned such that there is at least one closed row (10, 12) of staples on the outside of the cutting edge. It can be moved towards the anvil. The line along which the closed row (10, 12) of staples is arranged has a stepped shape, leaving a plane perpendicular to the longitudinal axis of the staple fastening assembly, such that this line has a larger total length than the projection of this line onto this plane. This provides a greater flexibility of the anastomotic site and less tension during instrument removal, alleviating the incidence of clinical complications.

14 Claims, 5 Drawing Sheets

SURGICAL STAPLING INSTRUMENT

BACKGROUND OF THE INVENTION

The invention relates to a surgical stapling instrument, which can be used for applying surgical staples or clips to tissue and in particular for performing an anastomosis.

Generally, in the performance of a surgical anastomotic stapling operation, two pieces of lumen or tubular tissue, e.g., intestinal tissue, are attached together by a closed row of staples. In performing the anastomosis with a surgical stapling instrument, the two pieces of tubular tissue are clamped together between an anvil provided with an array of staple forming grooves and a staple holder or cartridge device provided with a plurality of staple receiving slots arranged in a closed row or array in which the staples are received. A staple pusher is advanced to drive the staples into the tissue and form the staples against the anvil. Moreover, a circular knife is advanced to cut the excess tissue clamped between the anvil and the staple holder. As a result, the donut-shaped section of tissue is severed from each lumen and remains on the anvil shaft. The tubular tissue joined by the closed row of staples is unclamped by moving the anvil relative to the staple holder, usually by advancing the anvil shaft distally to move the anvil away from the staple holder. The stapling instrument is removed by pulling the anvil through the opening between the pieces of tubular tissue attached by the array of staples.

Surgical stapling instruments of this kind are well-known. For example, U.S. Pat. No. 5,205,459 describes such an instrument in detail. As usual, the closed row of staples of the instrument disclosed has a planar, circular shape. U.S. Pat. No. 5,275,322 is a document showing a basic version of a circular stapling instrument.

Although the use of the known surgical stapling instruments is very beneficial and greatly facilitates the performance of an anastomosis, it involves some problems. Often it is difficult to retract the instrument from the site of the operation, because it is difficult to move the anvil through the opening bordered by the closed row of staples, which is somewhat stiff. Moreover, after the operation, the incidence of clinical stenosis at the site of the anastomosis is not rare.

In order to overcome these problems, it is proposed in WO 01/54594 A1 to arrange the closed row of staples in a wavy shape which leaves a plane perpendicular to the longitudinal axis of the instrument. In this way, the line along which the staples of the closed row are arranged has a larger total length than the projection of this line onto a plane. Consequently, the length of an anastomosis seam is larger than that of an anastomosis performed by means of conventional stapling instrument. Because of this increased length, the anastomotic site can assume a larger diameter and is more flexible, so that the anvil can be easily moved through the opening created by the knife, and the surgical stapling instrument can be retracted at the end of the surgery more easily. Additionally, the resulting larger anastomosis lumen will alleviate the incidence of clinical complications. On the other hand, if it is sufficient that the total length of the closed row of staples is comparable to that provided by a conventional stapling instrument, this instrument can be designed in a more compact size such that it can be easier inserted into a tubular organ and removed therefrom.

For optimum performance of the stapling instrument disclosed in WO 01/54594 A1, the individual staples are expelled from the cartridge device in a direction perpendicular to the local slope of the wavy shape, which generally is not parallel to the longitudinal axis of the instrument. This requires a more complicated staple drive mechanism which experiences load components transverse to the longitudinal axis of the instrument. Moreover, the alignment of the staple-forming grooves at the anvil to the pointed ends of the staples exiting from the cartridge device is only correct for a certain distance between the cartridge device and the anvil, i.e. for a certain thickness of the tissue clamped between the cartridge device and the anvil, which results in a loss of variability with respect to the tissue thickness.

EP 1 090 592 A1 discloses a linear surgical stapler, in which the anvil has two staple-forming surfaces which are spaced with respect to each other in the staple expelling direction. In this way, the anvil is formed with a stiffening rib which generally strengthens the cantilever design of the linear stapler.

BRIEF SUMMARY OF THE INVENTION

The object of the invention is to provide a surgical stapling instrument for performing an anastomosis, which has the advantages of the instrument disclosed in WO 01/54594 A1, but allows for a simpler design and generally exhibits less restrictions with respect to tissue thickness.

The surgical stapling instrument according to the invention comprises a frame having a body portion and a handle as well as a staple fastening assembly in the distal region of the instrument. The staple fastening assembly includes a cartridge device which comprises at least one closed row of staples, and an anvil. The anvil is movable relative to the cartridge device and is adapted to cooperate with the cartridge device for forming the ends of the staples exiting from the cartridge device. A moving device is adapted to move the anvil relative to the cartridge device. A staple driving device is adapted to drive the staples out of the cartridge device towards the anvil. A knife, which has a closed cutting edge, is contained within the cartridge device and is positioned such that there is at least one closed row of staples on the outside of the cutting edge. A knife actuating device is adapted to move the knife towards the anvil. So far, these features are known from the prior art, e.g., from U.S. Pat. No. 5,205,459.

According to the invention, the line along which the closed row of staples is arranged has a stepped shape, leaving (i.e. not being confined to) a plane perpendicular to the longitudinal axis of the staple fastening assembly, such that said line has a larger total length than the projection of said line onto said plane. Preferably, this projection is circular.

Thus, the line along which the closed row of staples is arranged has a larger total length than the line defining the planar array of staples of a conventional prior art surgical stapling instrument in which the cartridge device has about the same size. Consequently, similar to the instrument disclosed in WO 01/54594 A1, the length of the anastomosis seam is larger than that of an anastomosis performed by means of a conventional stapling instrument. Because of this increased length, the anastomotic site can assume a larger diameter and is more flexible, so that the anvil can be easily removed through the opening created by the knife, and the surgical stapling instrument can be retracted at the end of the surgery more easily. Additionally, the resulting larger anastomosis lumen will alleviate the incidence of clinical complications. On the other hand, if it is sufficient that the total length of the line along which the closed row of staples is arranged is comparable to that provided by a conventional stapling instrument, the invention allows for the use of a smaller instrument, which generally can be more easily inserted into the tubular organ and removed therefrom.

So far, the advantages of the surgical stapling instrument according to the invention are similar to those of the instrument disclosed in WO 01/54594 A1.

Additional advantages result from the stepped shape of the line along which the closed row of staples is arranged. In particular, this allows for a design in which a local flat area, which is normal to the longitudinal axis of the instrument, is created for each staple. By applying a simple conventional axial drive mechanism, the staple driving device can be adapted to drive the staples out of the cartridge device such that each staple is moved essentially in parallel to the longitudinal axis of the staple fastening assembly, which is the optimum direction in view of the stepped shape of the closed row of staples. Such kind of drive mechanism avoids undesired transverse loads. Moreover, the pointed ends of staples exiting from the cartridge device stay aligned to the staple-forming grooves provided at the anvil, irrespective of the actual distance between the anvil and the cartridge device or the thickness of the tissue clamped between the anvil and the cartridge device. In other words, any anvil deflection or any staple height adjustability will not adversely effect staple location. When a simple axial drive mechanism is employed, the stroke or actuating behaviour of conventional instruments can be maintained, which is an advantage because surgeons are familiar with it. Finally, the invention allows for the application of existing circular stapler platforms, i.e. of existing components like frame, moving device, and staple driving device, and therefore saves considerable costs.

Preferably, the anvil has a stepped staple-forming surface which matches the stepped shape of the line along which the closed row of staples is arranged.

Whereas it is conceivable that the knife has a conventional (cylindrical) basic shape with a circular cutting edge, in a preferred version of the invention the line defining the cutting edge of the knife has a stepped shape and runs essentially in parallel to the line along which the closed row of staples is arranged. In this design, the knife has to be moved by a short distance only in order to completely cut the tissue clamped between the cartridge device and the anvil.

In an advantageous version of the invention, the staples of a closed row of staples are arranged at different positions, measured along the longitudinal axis of the staple fastening assembly. In this way, the staples are located at different steps of the stepped shape of the closed row of staples. Alternatively, or with respect to another closed row of staples, the staples of a closed row of staples can be arranged with gaps between adjacent staples, wherein each gap is defined by a recess in the surface of the cartridge device, and the anvil has a protrusion fitting into that recess. Or the staples can be arranged with protrusions between adjacent staples, wherein each protrusion emerges from the surface of the cartridge device, and the anvil has a recess for accommodating that protrusion. A corresponding closed row of staples having both protrusions and gaps or recesses between different pairs of adjacent staples is conceiveable as well. Thus, the line along which such closed rows of staples are arranged has a stepped shape, since this line also follows the gaps or protrusions, although the staples themselves may be located all in the same plane.

As already mentioned, in a preferred version of the invention, the staple driving device is adapted to drive the staples out of the cartridge device such that each staple is moved essentially in parallel to the longitudinal axis of the staple fastening assembly. This allows for a simple, reliable and less expensive design of the surgical stapling instrument. Preferably, the staple driving devices comprises pushers for driving the staples. For adjustment to the stepped shape of the closed row of staples, the pushers can have different lengths. In an advantageous version, the pushers are integrally combined in a sleeve structure. Providing pushers of different lengths allows for a simple design in which the staple driving device is adapted to drive the staples of a closed row of staples essentially simultaneously out of the cartridge device. Such actuating behaviour maintains the stroke of a conventional stapling instrument.

Preferably, there are at least two closed rows of staples, wherein the staples of adjacent rows are staggered with respect to each other. The staggered arrangement of the staples does not contradict the basic idea of the stepped shape of the closed rows of staples, which will become evident from the embodiment described below in more detail. An anastomosis seam containing two rows of staggered staples is tight and safe.

The anvil can comprise a counterpart adapted to accommodate the cutting edge of the knife. The counterpart preferably matches the stepped shape of the anvil and/or the knife. Such counterparts, which exert a reaction force onto the tissue during the cutting action and are cut by the knife, are generally known in the prior art, see, e.g., U.S. Pat. No. 4,289,133.

In an advantageous version of the invention, the staple fastening assembly is removably mounted in the distal end region of the body portion. This enables, e.g., the staple fastening assembly to be exchanged during the surgical operation or to be designed as a disposable part (whereas the frame including a major part of the mechanical components is sterilizable and reusable). Moreover, the cartridge device can comprise a removable cartridge containing the staples, such that, e.g., an empty cartridge can be replaced by a fresh one, if required, or the cartridge device can be designed as a re-usable component. Preferably, the anvil is removable as well, which is also essential for certain surgical techniques. To this end, the anvil can comprise a shaft fitting onto a peg protruding from the cartridge device. The peg preferably comprises a mandrel which is useful for piercing tissue in certain surgical techniques. These features are generally known from the prior art surgical stapling instruments.

The term "staple" is used herein in a very general sense. It includes metal staples or clips, but also surgical fasteners made of synthetic material and similar fasteners. Synthetic fasteners usually have a counterpart (retainer member) held at the anvil. In this sense, the term "anvil" also has a broad meaning which includes, in the case of two-part synthetic fasteners, the anvil-like tool where the retainer members are held, and similar devices.

BRIEF DESCRIPTION OF THE DRAWINGS

In the following, the invention is described in more detail by means of an embodiment. The drawings show in FIG. 1 a side view of the staple fastening assembly of an embodiment of the surgical stapling instrument according to the invention, FIG. 2 an isometric view onto an end part which forms the distal surface of the cartridge device of the staple fastening assembly of FIG. 1, FIG. 3 an isometric view of the distal portion of the staple driving device of the embodiment, FIG. 4 an isometric view onto the staple-forming surface of the anvil of the embodiment of the stapling instrument, FIG. 5 an isometric view onto the staple-forming surface of the anvil of another embodiment of the stapling instrument.

Figure 1:
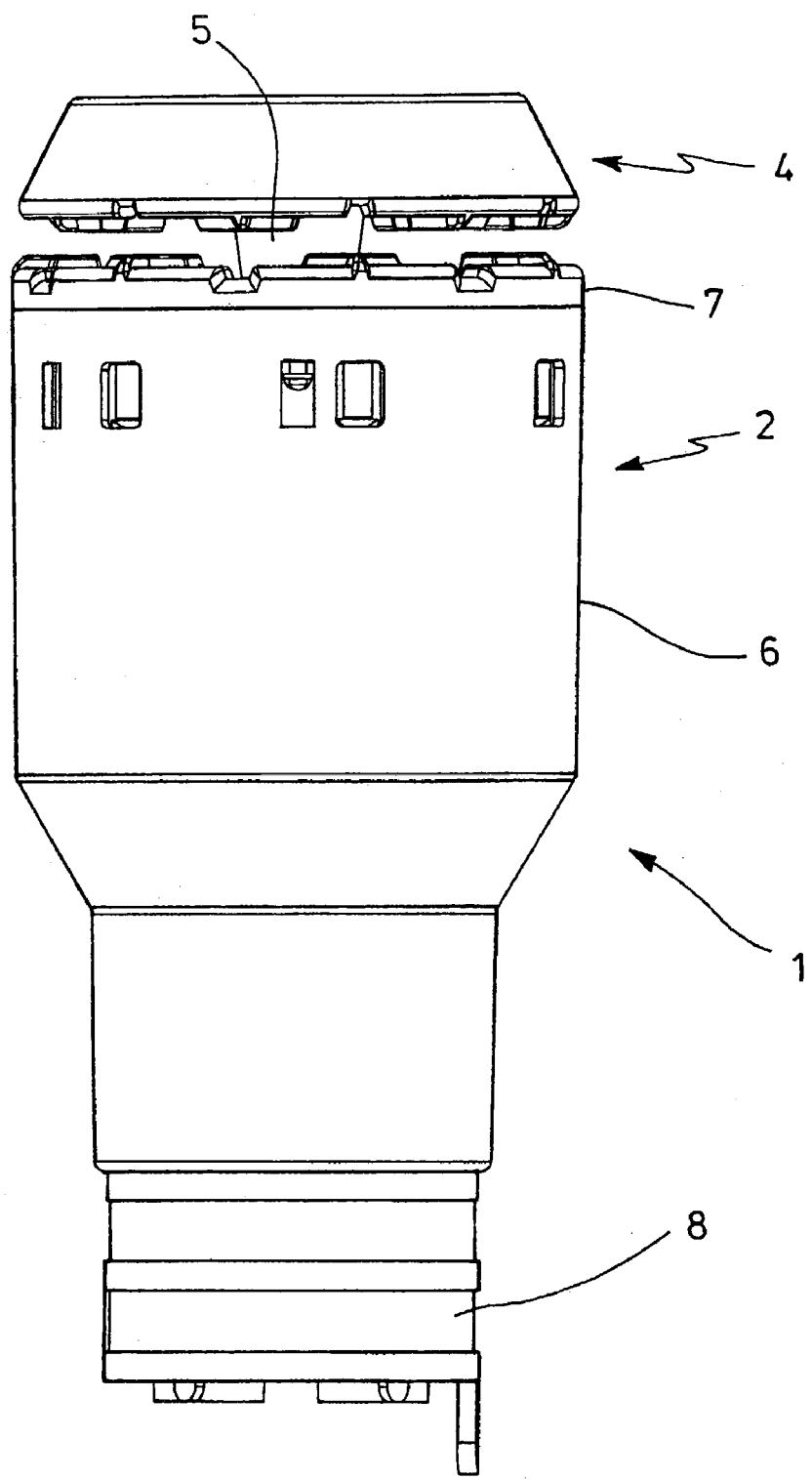
FIG. 1 is a side view of the staple fastening assembly 1 which forms the distal portion of a surgical stapling instrument. The staple fastening assembly 1 includes a cartridge device 2 (which comprises, in the embodiment, two closed rows of staples) and an anvil 4. The anvil 4 is mounted at the distal end of a shaft 5 and can be moved relative to the cartridge device 2, i.e. along the longitudinal axis of the staple fastening assembly 1, in order to adjust the size of the gap between the anvil 4 and the cartridge device 2.

The cartridge device 2 comprises a housing 6 which contains the staples, a circular knife, as well as components of a moving device (adapted to move the anvil 4 relative to the cartridge device 2), a staple driving device (adapted to drive the staples out of the cartridge device 2 towards the anvil 4), and a knife actuating device (adapted to move the knife towards the anvil 4). The end face of the cartridge device 2, i.e. the surface from which the staples exiting from the cartridge device 2 are expelled towards the anvil 4, is formed in an end part 7 inserted into the circumferential wall of the housing 6.

The staple fastening assembly 1 can be removably mounted on a shaft of the stapling instrument by means of a coupling 8 provided at the proximal end region of the cartridge device 2. The terms "proximal" and "distal" relate to the view of the person operating the stapling instrument.

Generally, the overall design and the mechanical components, drive mechanisms and safety features of the surgical stapling instrument are as in a conventional circular stapling instrument; the three-dimensional shape of the staple lines and some details of the staple driving device, however, are different, as explained in the following.

Figure 2:
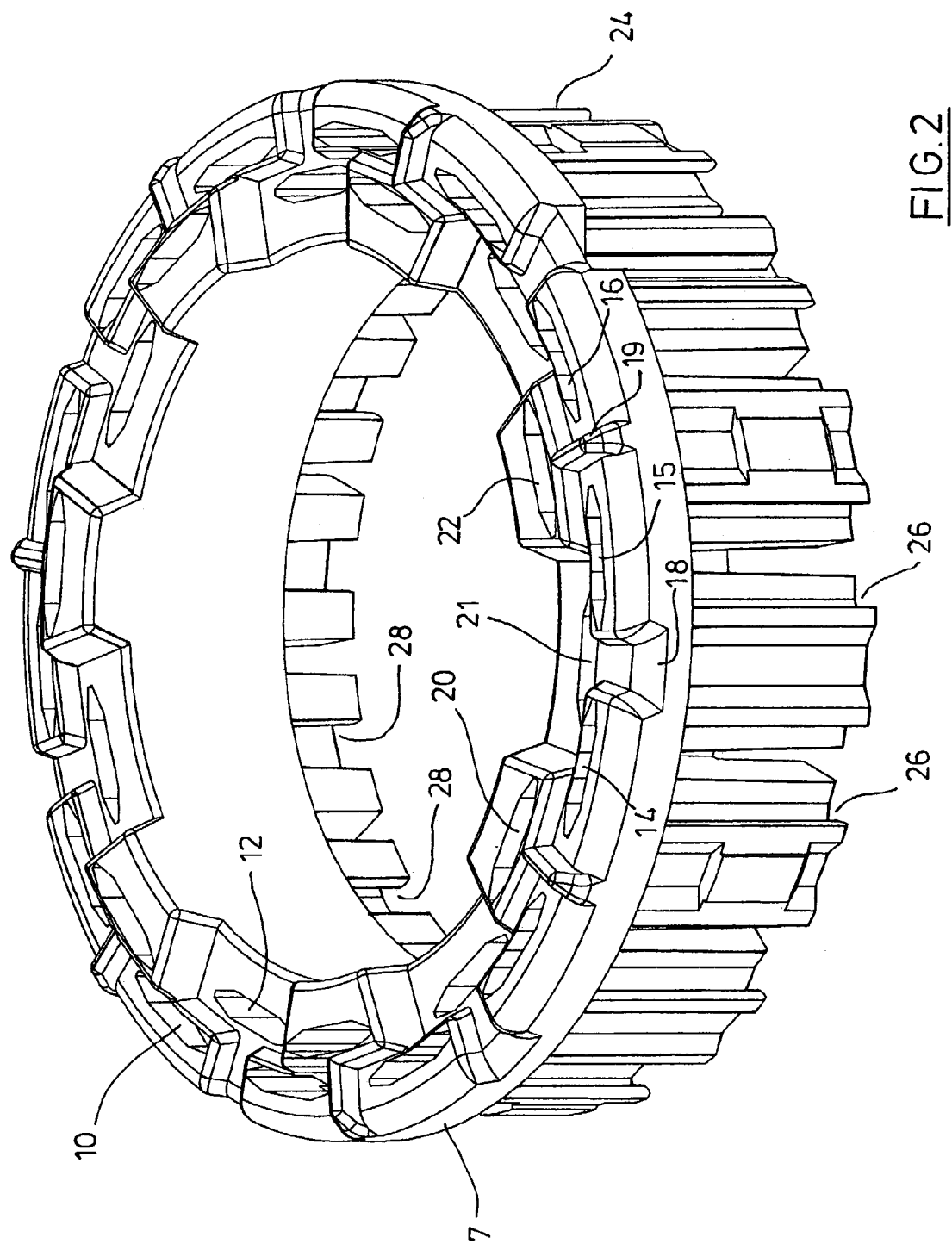

FIG. 2 shows the end part 7 in an isometric view. The distal surface of the end part 7 comprises slots from which the staples are expelled towards the anvil 4 when the stapling instrument is "fired". These slots are arranged in two closed rows, thus defining a first closed row 10 of staples (the outer one in FIG. 2) and a second closed row 12 of staples (the inner one in FIG. 2).

Three of these exit slots of the first closed row 10 are designated by the reference numerals 14, 15, and 16. As shown in FIG. 2, the exit slots 14, 15, and 16 and all the other exit slots of the first closed row 10 lie in the same plane, i.e. a plane perpendicular to the longitudinal axis of the staple fastening assembly 1. Between the exit slots 14 and 15, there is a gap or recess 18, whereas a protrusion 19 emerges from the area between the exit slots 15 and 16. This pattern is repeated along the circumference of the first closed row 10. In this way, the line along which the first closed row 10 of staples is arranged, i.e. the line around the first closed row 10 following the surface topography of the end part 7 and descending into the recess 18 and ascending around the protrusion 19, has a stepped shape. It is this line which defines, in the area of the first closed row 10, the tissue contact between the cartridge device 2 and the anvil 4 when the stapling instrument is operated.

In a similar manner, the line along which the second closed row 12 of staples is arranged has a stepped shape as well. In this case, however, the exit slots of the staples are located in two different planes, each perpendicular to the longitudinal axis of the staple fastening assembly 1. As shown in FIG. 2, exit slots 20 and 22 are in the same plane which is more distal than the plane of the exit slots of the first closed row 10. Exit slot 21, which is arranged between the exit slots 20 and 22, is located in the other plane and is more proximal than the exit slots of the first closed row 10. This pattern is repeated along the circumference of the second closed row 12. In the embodiment, the peaks of the protrusions 19 are in the plane of the exit slots 20 and 22, whereas the grounds of the recesses 18 are in the plane of exit slot 21. Exit slot 21 and the corresponding exit slots of the second closed row 12 are radially aligned with the recesses 18. As shown in FIG. 2, the staples of the first closed row 10 and the staples of the second closed row 12 are staggered with respect to each other.

In FIG. 2, a staple guide part 24 is located below the distal surface of the end part 7. The staple guide part 24 comprises guide slots 26 for guiding the staples of the first closed row 10 and guide slots 28 for guiding the staples of the second closed row 12. Each of theses guide slots 26, 28 accommodates one staple, the pointed ends of the staple facing the corresponding exit slot. The staple guide part 24 as well as the end part 7 are preferably made of a medical grade resin by injection moulding and may be manufactured as one component.

The circular knife, which is not shown in the figures, is guided at the inner periphery of the end part 7. It is moved in distal direction when the stapling instrument is actuated, as usual with conventional circular staplers. In the embodiment, the cutting edge of the knife has a stepped shape which essentially follows the stepped shape of the line along which the second closed row 12 of staples is arranged.

Figure 3:
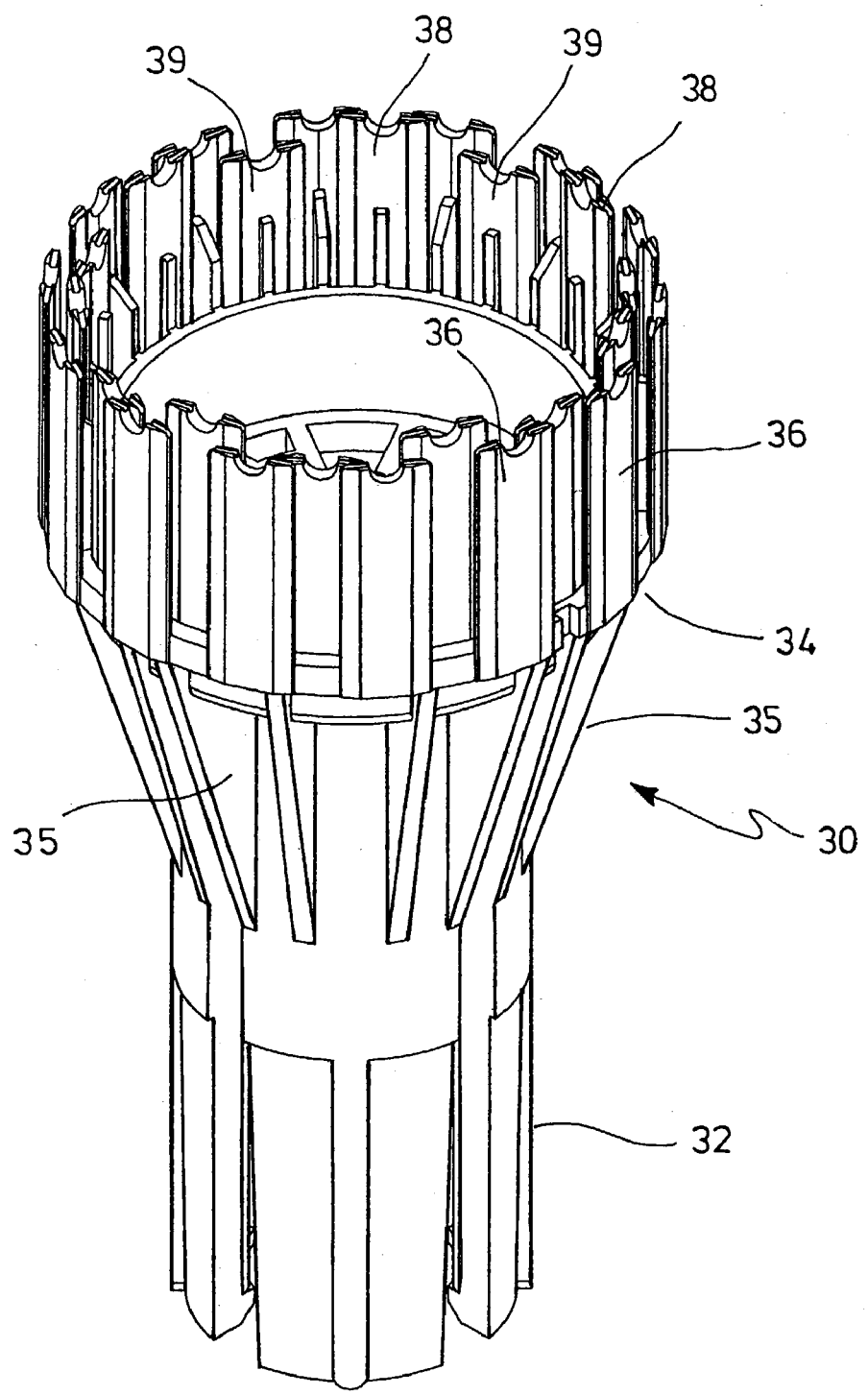

FIG. 3 shows the distal portion 30 of the staple driving device of the stapling instrument. In the embodiment, this portion is designed as an integrally moulded sleeve structure. It includes an actuator shaft 32 distally ending at a base 34 which is reinforced by means of ribs 35. The proximal end of the actuator shaft 32 is coupled to an actuating rod inside the shaft of the stapling instrument when the staple fastening assembly 1 is mounted to the distal end of this shaft. When the instrument is "fired", i.e. when an actuating trigger located at the handle of the instrument is operated, the actuating rod is moved in distal direction, thus pushing the sleeve structure 30 in distal direction as well.

For each staple, the staple driving device 30 comprises a pusher protruding in distal direction and parallel to the longitudinal axis of the staple fastening assembly 1. These pushers are arranged in two rows, i.e. the outer pushers 36 for the first closed row 10 of staples and the inner pushers 38 and 39 for the second closed row 12 of staples. In the assembled state of the staple fastening assembly 1, the pushers 36 are guided in the guide slots 26, whereas the pushers 38 and 39 are guided in the guide slots 28. As shown in FIG. 3, all of the pushers 36 have the same length, but the pushers 39 are shorter than the pushers 38. The end side of each pusher 36, 38 and 39 abuts at the crown of a staple such that the staples are expelled from the exit slots of the first closed row 10 and the second closed row 12 when the instrument is fired.

The shorter pushers 39 are assigned to exit slot 21 and the corresponding exit slots of the second closed row 12, whereas the longer pushers 38 are assigned to the exit slots 20, 22 and the other exit slots in the more distal plane for the second closed row 12. The length of the pushers 36 is between that of the pushers 38 and 39, corresponding to the location of the exit slots of the first closed row 10. This design results in an almost simultaneous exit of all staples from their exit slots when the instrument is fired.

Figure 4:
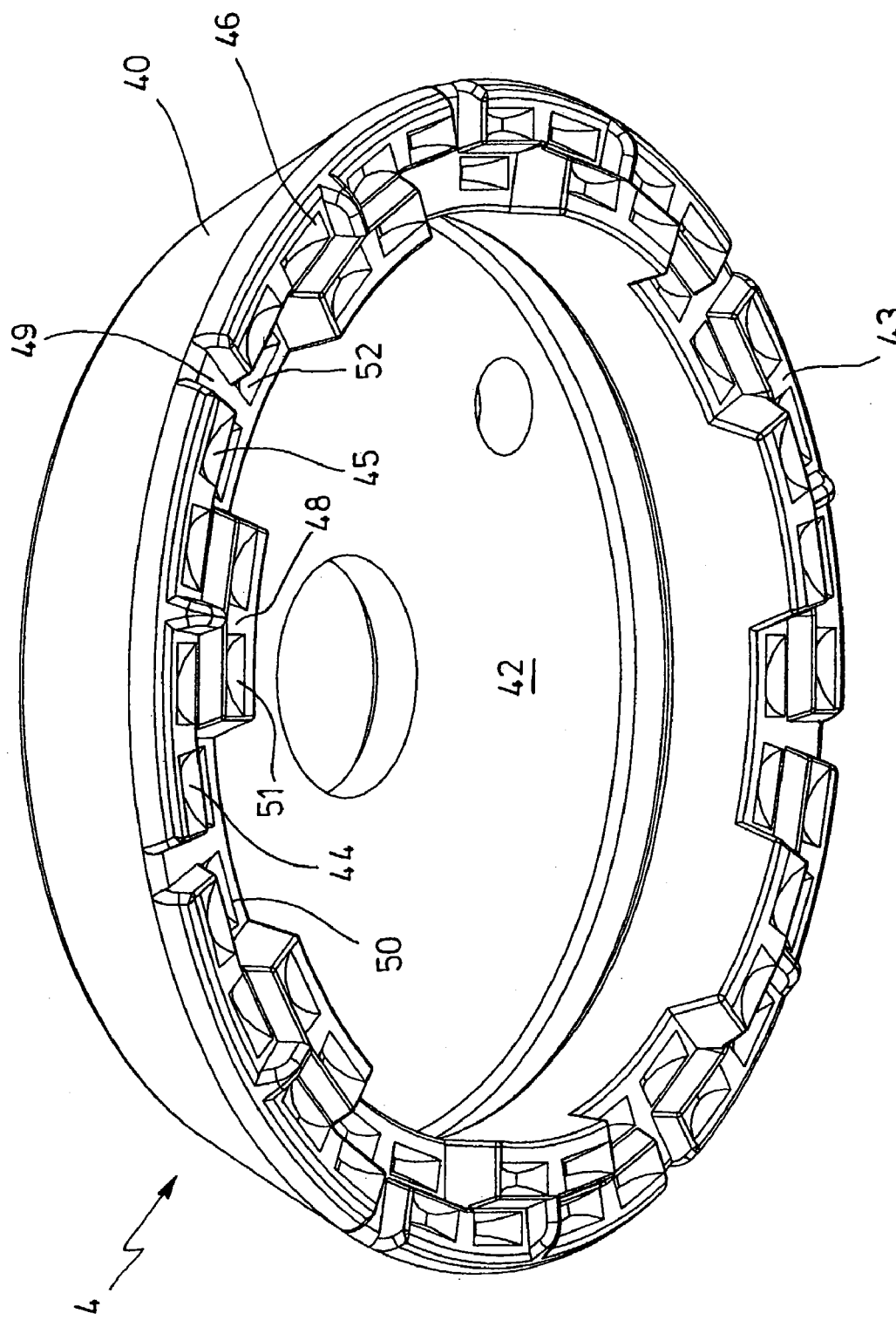

FIG. 4 is an isometric view onto the proximal surface of the anvil 4, which includes a peripheral rim 40 and an end plate 42. The proximal end side of the rim 40 is designed as a staple-forming surface 43. For each staple, the staple-forming surface 43 comprises a pair of staple-forming grooves which form or bend the pointed ends of the staple when these ends are pushed against the staple-forming surface 43 upon firing the instrument.

The relief of the staple-forming surface 43 is essentially a negative of the relief of the end surface of end part 7. Thus, in the mounted state of the anvil 4, the grooves 44, 45, and 46 match to the exit slots 14, 15, and 16 of the first closed row 10, and a protrusion 48 between the grooves 44 and 45 fits into the recess 18, whereas a recess 49 accommodates the protrusion 19 when the anvil 4 is close to the cartridge device 2. Similarly, the locations of grooves 50, 51, and 52 match to the positions of the exit slots 20, 21, and 22 of the second closed row 12.

Generally, the stapling instrument is operated like a conventional circular stapler. By moving the anvil 4 towards the cartridge device 2, the tissue ends to be stapled are clamped between the end surface of end part 7 and the staple-forming surface 43 of the anvil 4. The tissue follows the stepped shapes of the lines along which the first closed row 10 and the second closed row 12 of staples are arranged and is forced by protrusions like the protrusion 48 or the staple-forming surface 51 on the anvil 4 into corresponding recesses like the recess 18 or the area of the exit slot 21, and vice versa. The width of the recesses like recess 49 or recess 18 is somewhat larger than the width of the corresponding protrusions like protrusion 19 or protrusion 48, such that the tissue is not squeezed in the protrusion/recess pairs.

When the instrument is fired, the staples of the first closed row 10 and the second closed row 12 are expelled almost simultaneously from the end surface of the end part 7, penetrate the tissue parts and are formed at the staple-forming surface 43 of the anvil 4. Immediately afterwards, the cutting edge of the circular knife, which is mounted on the staple driving device 30 inside the pushers 38 and 39 of the second closed row 12, cuts the tissue.

After firing, the distance between the anvil 4 and the cartridge device 2 is somewhat increased in order to release the anastomosis seam. Because of the stepped structures of the end surface of the end part 7 and the staple-forming surface 43 of the anvil 4, the staple lines of the anastomosis seam have a greater length than comparable staple lines resulting from corresponding smooth surfaces in a conventional circular stapler of the same outer diameter. Consequently, retraction of the instrument is easier.

Figure 5:
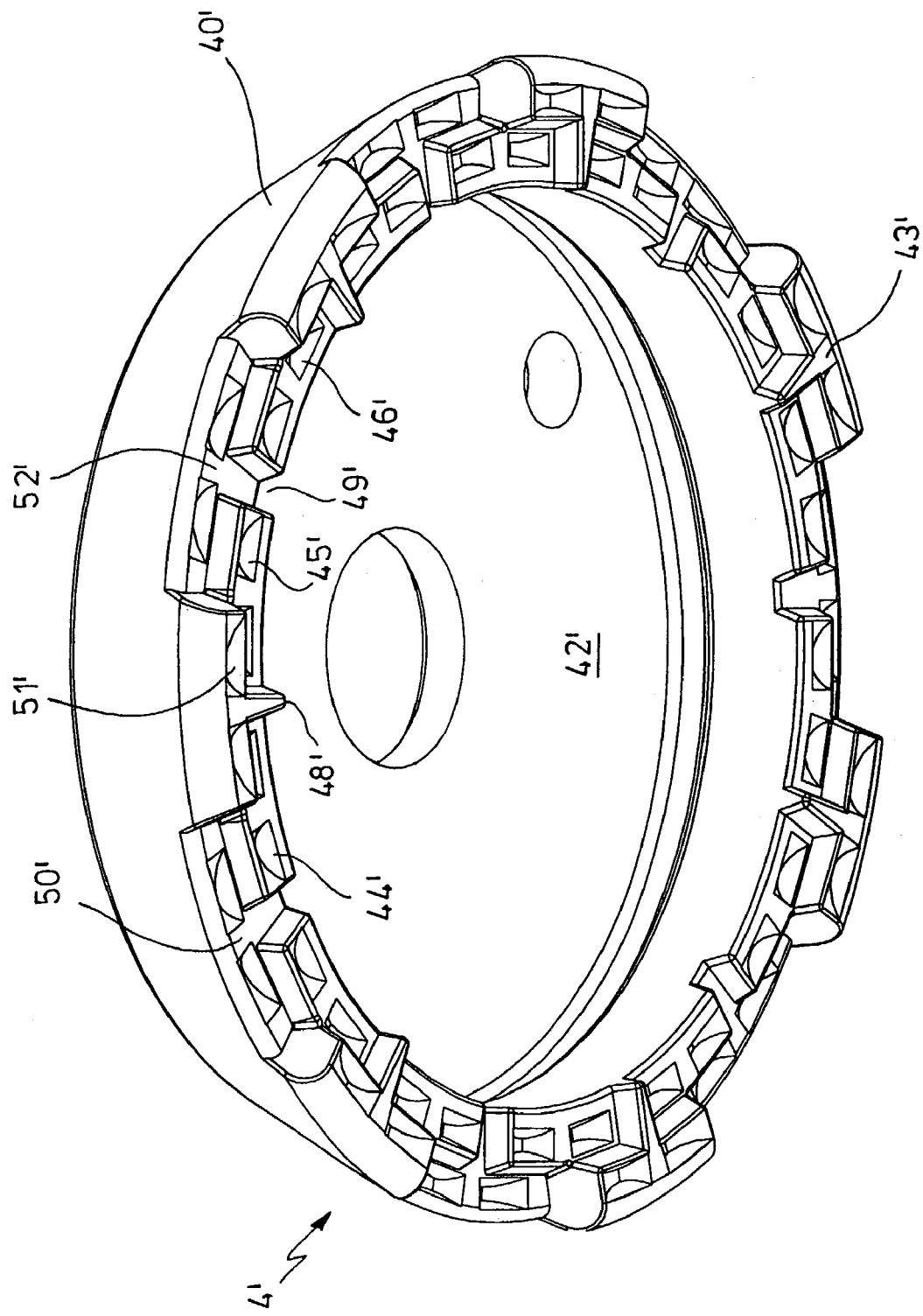

FIG. 5 is an isometric view onto the proximal surface of the anvil 4' of a second embodiment of the surgical stapling instrument. The anvil 4' is the counterpart of a cartridge device having two closed raws of staples, in which the designs of the outer closed raw of staples and of the inner closed raw of staples are reversed with respect to the cartridge device 2 of the first embodiment. To facilitate comparison with FIG. 4, in FIG. 5 the same reference numerals are used as in FIG. 4, but they are primed.

The relief of the staple-forming surface 43' is essentially a negative of the relief of the end surface of the cartridge device of the second embodiment. In a corresponding staple driving device, the lengths of the pushers are adjusted to the locations of the staples in the cartridge device of the second embodiment. The cartridge device and the staple driving device of the second embodiment are not shown in the figures because the details are evident from a comparison with the first embodiment.

What is claimed is:

1. A surgical stapling instrument having a distal end, a proximal end, and a longitudinal axis therebetween, said instrument comprising:
 a flame having a body portion and a handle,
 a staple fastening assembly (1) in the distal region of said instrument, the staple fastening assembly (1) including a cartridge device (2), said cartridge having a distal surface having a stepped configuration comprising a series of alternating gaps and protrusions such that said protrusions are distal to said gaps, said cartridge device further comprising at least one closed row (10, 12) of staples disposed along said series of alternating gaps and protrusions, and an anvil (4) which is movable relative to the cartridge device (2) and is adapted to cooperate with the cartridge device (2) for forming the ends of the staples exiting from the cartridge device (2), a moving device adapted to move the anvil (4) relative to the cartridge device (2), a staple driving device adapted to drive the staples out of the cartridge device (2) towards the anvil (4), a knife, which has a closed cutting edge, is contained within the cartridge device (2) and is positioned such that there is at least one closed row (10, 12) of staples on the outside of the cutting edge, and a knife actuating device adapted to move the knife towards the anvil (4).

2. Stapling instrument according to claim 1, characterized in that the anvil (4) has a proximal surface having a stepped configuration comprising a series of alternating gaps and protrusions which matches the stepped configuration cartridge, such that said gaps on said cartridge match said protrusions on said anvil, and said protrusions on said cartridge match said gaps on said anvil.

3. Stapling instrument according to claim 1, characterized in that said knife has a stepped shape which matches the stepped configuration of said distal surface of said cartridge.

4. Stapling instrument according to claim 1, characterized in that the staple driving device (30) is adapted to drive the staples out of the cartridge device (2) such that each staple is moved essentially in parallel to the longitudinal axis of the staple fastening assembly (1).

5. Stapling instrument according to claim 4, characterized in that the staple driving device (30) comprises pushers (36, 38, 39) for driving the staples.

6. Stapling instrument according to claim 5, characterized by at least two groups of pushers (38, 39) having different lengths.

7. Stapling instrument according to claim 5 or 6, characterized in that the pushers (36, 38, 39) are integrally combined in a sleeve structure (30).

8. Stapling instrument according to claim 1, characterized in that the staple driving device (30) is adapted to drive the staples of a closed row (10, 12) of staples essentially simultaneously out of the cartridge device (2).

9. Stapling instrument according to claim 1, characterized by at least two closed rows (10, 12) of staples, wherein the staples of adjacent rows (10, 12) are staggered with respect to each other.

10. Stapling instrument according to claim 1, characterized in that the anvil (4) comprises a counterpart adapted to accommodate the cutting edge of the knife.

11. Stapling instrument according to claim 1, characterized in that the staple fastening assembly (1) is removably mounted in the distal end region of the body portion.

12. Stapling instrument according to claim 1, characterized in that the anvil (4) is removable.

13. Stapling instrument according to claim 12, characterized in that the anvil comprises a shaft fitting onto a peg protruding from the cartridge device, which peg preferably comprises a mandrel.

14. Stapling instrument according to claim 1, characterized in that the cartridge device (2) comprises a removable cartridge containing the staples.

* * * * *